United States Patent
Li et al.

(10) Patent No.: US 11,559,592 B2
(45) Date of Patent: Jan. 24, 2023

(54) STERILIZATION STRUCTURE, STERILIZATION BOARD AND DISPLAY DEVICE

(71) Applicants: Hefei Xinsheng Optoelectronics Technology Co., Ltd., Anhui (CN); BOE Technology Group Co., Ltd., Beijing (CN)

(72) Inventors: Guangyao Li, Beijing (CN); Luke Ding, Beijing (CN); Leilei Cheng, Beijing (CN); Yingbin Hu, Beijing (CN); Jingang Fang, Beijing (CN); Ning Liu, Beijing (CN); Qinghe Wang, Beijing (CN); Dongfang Wang, Beijing (CN); Liangchen Yan, Beijing (CN)

(73) Assignees: Hefei Xinsheng Optoelectronics Technology Co., Ltd., Anhui (CN); BOE Technology Group Co., Ltd., Beijing (CN)

( * ) Notice: Subject to any disclaimer, the term of this patent is extended or adjusted under 35 U.S.C. 154(b) by 727 days.

(21) Appl. No.: 16/442,860

(22) Filed: Jun. 17, 2019

(65) Prior Publication Data

US 2020/0155717 A1    May 21, 2020

(30) Foreign Application Priority Data

Nov. 19, 2018    (CN) .......................... 201811375954.5

(51) Int. Cl.
*A61L 2/03*    (2006.01)
*C01B 32/182*    (2017.01)

(52) U.S. Cl.
CPC ............ *A61L 2/035* (2013.01); *C01B 32/182* (2017.08)

(58) Field of Classification Search
CPC ...... A61L 2/035; A61L 2202/11; A61L 2/232; A61L 2/03; C01B 32/182; H01L 29/1606; H01L 29/78684
See application file for complete search history.

(56) References Cited

U.S. PATENT DOCUMENTS

| 8,742,478 | B2 | 6/2014 | Chung et al. |
| 10,141,409 | B2* | 11/2018 | Zhang .................. H01L 27/124 |
| 2011/0092054 | A1 | 4/2011 | Seo et al. |
| 2015/0364567 | A1* | 12/2015 | Feng ................. H01L 29/42364 |
| | | | 438/151 |

(Continued)

FOREIGN PATENT DOCUMENTS

| CN | 103094346 A | 5/2013 |
| CN | 105304495 A | 2/2016 |

OTHER PUBLICATIONS

Swatantra, Laser-Induced Graphene Layers and Electrodes Prevents Microbial Fouling and Exterts Microbial Action (Year: 2017).*

(Continued)

*Primary Examiner* — Sean E Conley
*Assistant Examiner* — Brendan A Hensel
(74) *Attorney, Agent, or Firm* — Banner & Witcoff, Ltd.

(57) ABSTRACT

A sterilization structure, a sterilization board, and a display device are disclosed. The sterilization structure includes an active layer, wherein, one surface of the active layer has an exposed region, and a material of the active layer includes a laser-induced graphene material.

9 Claims, 3 Drawing Sheets

(56) References Cited

U.S. PATENT DOCUMENTS

2020/0343054 A1* 10/2020 Gadiwan ............... H01G 11/32

OTHER PUBLICATIONS

S.P. Singh, et al., "Laser-Induced Graphene Layers and Electrodes Prevents Microbial Fouling and Exerts Antimicrobial Action", ACS Applied Materials & Interfaces, May 18, 2017, pp. 18238-18247.
May 25, 2021—(CN) First Office Action Appn 201811375954.5 with English Translation.

* cited by examiner ature further includes a source electrode layer; and a drain electrode layer, the source electrode layer and the drain electrode layer are disposed independently of each other, and are respectively electrically connected with the active layer.
STERILIZATION STRUCTURE, STERILIZATION BOARD AND DISPLAY DEVICE

CROSS-REFERENCE TO RELATED APPLICATIONS

The present application claims priority of Chinese Patent Application No. 201811375954.5 filed on Nov. 19, 2018, the disclosure of which is incorporated herein by reference in its entirety as part of the present application.

TECHNICAL FIELD

Embodiments of the present disclosure relate to a sterilization structure, a sterilization board and a display device.

BACKGROUND

In recent years, with rapid development of artificial intelligence, flexible display, transparent display and environmental detection, displays for different uses have received more and more attention, and people's requirements for performance of the displays also develop from traditional display to multi-functional display.

SUMMARY

At least one embodiment of the present disclosure provides a sterilization structure, the sterilization structure includes an active layer, a surface of the active layer includes an exposed region, and a material of the active layer includes a laser-induced graphene material.

For example, in the sterilization structure provided by an embodiment of the present disclosure, the sterilization structure further includes a source electrode layer; and a drain electrode layer, the source electrode layer and the drain electrode layer are disposed independently of each other, and are respectively electrically connected with the active layer.

For example, in the sterilization structure provided by an embodiment of the present disclosure, at least one of the source electrode layer and the drain electrode layer includes a graphene material.

For example, in the sterilization structure provided by an embodiment of the present disclosure, the source electrode layer includes a first connecting portion connected with the active layer, the drain electrode layer includes a second connecting portion connected with the active layer, and an orthographic projection of at least one of the first connecting portion and the second connecting portion on the active layer falls into the exposed region.

For example, in the sterilization structure provided by an embodiment of the present disclosure, the sterilization structure further includes: a substrate; a gate electrode, located on the substrate; and a gate insulating layer, located on a side of the gate electrode away from the substrate, the active layer is located on a side of the gate insulating layer away from the gate electrode, and an orthographic projection of the active layer on the substrate at least partially overlaps with an orthographic projection of the gate electrode on the substrate.

For example, in the sterilization structure provided by an embodiment of the present disclosure, the first connecting portion is located between the active layer and the gate insulating layer, and the second connecting portion is located on a side of the active layer away from the substrate.

For example, in the sterilization structure provided by an embodiment of the present disclosure, the first connecting portion and the second connecting portion are both located between the active layer and the gate insulating layer.

For example, in the sterilization structure provided by an embodiment of the present disclosure, the first connecting portion is located on a side of the active layer away from the substrate, and the second connecting portion is located between the active layer and the gate insulating layer.

For example, in the sterilization structure provided by an embodiment of the present disclosure, the first connecting portion and the second connecting portion are disposed in different layers.

For example, in the sterilization structure provided by an embodiment of the present disclosure, materials of the source electrode layer, the drain electrode layer and the gate electrode all include a graphene material.

For example, in the sterilization structure provided by an embodiment of the present disclosure, a region of the surface of the active layer that is not covered by the source electrode layer and the drain electrode layer is the exposed region.

For example, in the sterilization structure provided by an embodiment of the present disclosure, the active layer has a thickness ranging from 20 microns to 25 microns.

At least one embodiment of the present disclosure provides a sterilization board, the sterilization board includes a plurality of sterilization structures according to any one of the above.

For example, in the sterilization board provided by an embodiment of the present disclosure, the plurality of sterilization structures are arranged in an array.

At least one embodiment of the present disclosure provides a display device, the display device includes the sterilization structure according to any one of the above.

For example, in the sterilization board provided by an embodiment of the present disclosure, the sterilization board further includes: a plurality of sterilization display elements arranged in an array, each of the plurality of sterilization display elements includes a display element and the sterilization structure.

BRIEF DESCRIPTION OF THE DRAWINGS

Hereinafter, the drawings accompanying embodiments of the present disclosure are simply introduced in order to more clearly explain technical solution(s) of the embodiments of the present disclosure. Obviously, the described drawings below are merely related to some of the embodiments of the present disclosure without constituting any limitation thereto.

DETAILED DESCRIPTION

Figure 1:
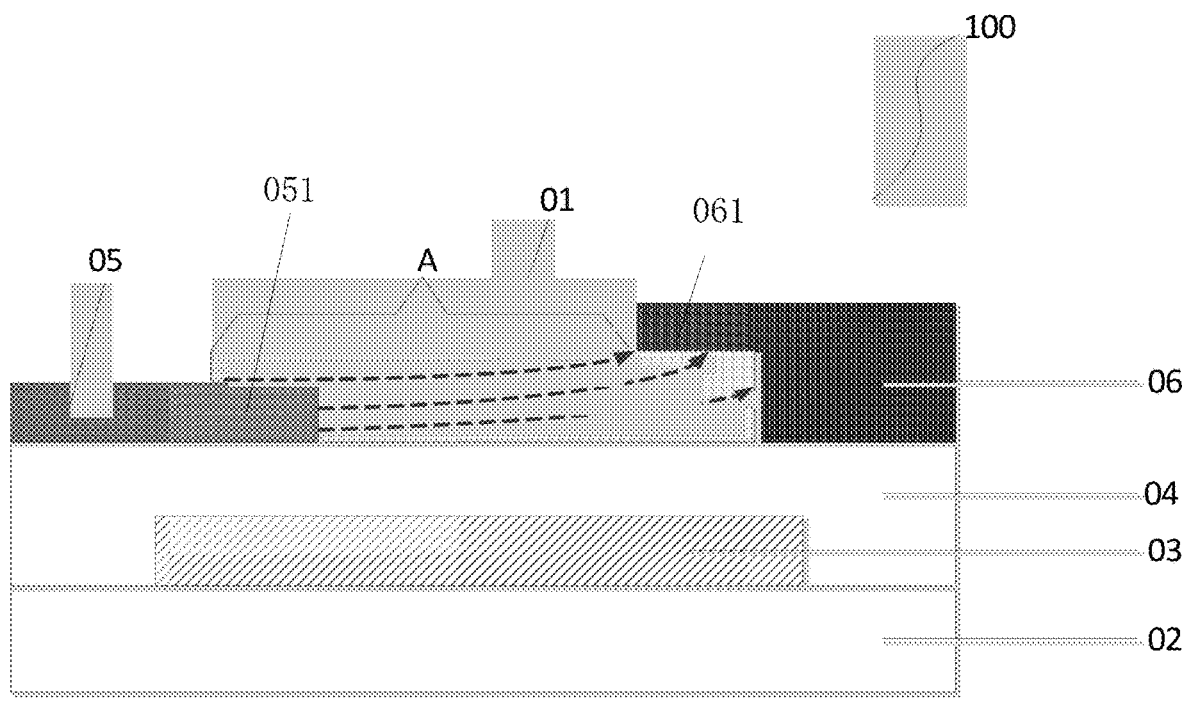
FIG. 1 is a structural schematic diagram of a sterilization structure provided by an embodiment of the present disclosure.

In order to make objects, technical details and advantages of the embodiments of the disclosure apparent, technical solutions according to the embodiments of the present disclosure will be described clearly and completely as below in conjunction with the accompanying drawings of embodiments of the present disclosure. Apparently, the described embodiments are only a part of but not all of exemplary embodiments of the present disclosure. Based on the described embodiments of the present disclosure, various other embodiments can be obtained by those of ordinary skill in the art without creative labor and those embodiments shall fall into the protection scope of the present disclosure.

Unless otherwise defined, the technical terminology or scientific terminology used herein should have the same meaning as commonly understood by one of ordinary skill in the art to which this disclosure belongs. The terms "first," "second," etc., which are used in the present disclosure, are not intended to indicate any sequence, amount or importance, but distinguish various components. Also, the terms "include," "including," "include," "including," etc., are intended to specify that the elements or the objects stated before these terms encompass the elements or the objects and equivalents thereof listed after these terms, but do not preclude the other elements or objects. The terms "connection", "connected" and the like are not limited to physical or mechanical connection but may include electrical connection, either directly or indirectly.

In the study, the inventor(s) of the present application finds that a display device will be contaminated and eroded by external bacteria, which, thus, affects a display effect and is not favorable for multi-functional display.

In this regard, embodiments of the present disclosure provide a sterilization structure, a sterilization board and a display device. The sterilization structure includes an active layer, a surface of the active layer includes an exposed region, and a material of the active layer includes a laser-induced graphene material. Thus, the sterilization structure, on the one hand, can puncture a cell membrane of a bacterium with a sharp surface of the laser-induced graphene material to kill the bacterium, and on the other hand, can also perform sterilization with electric charges on the active layer.

Hereinafter, the sterilization structure, the sterilization board and the display device provided by the embodiments of the present disclosure will be described in detail with reference to the accompanying drawings.

An embodiment of the present disclosure provides a sterilization structure. As shown in FIG. 1 to FIG. 4, the sterilization structure 100 includes an active layer 01. A surface of the active layer 01 includes an exposed region A, and the active layer 01 is made of a laser-induced graphene material. It should be noted that, the exposed region A of the active layer 01 is used to be in contact with outside environment and is configured to inhibit or kill bacteria on the exposed region A. In addition, the "bacteria" in the present disclosure include, but are not limited to, usual bacteria, and may also include microorganisms (for example, algae) that have an influence on human health or have an influence on display.

In the sterilization structure provided by the embodiment of the present disclosure, the surface of the active layer includes the exposed region, and the material of the active layer includes the laser-induced graphene material. In the exposed region of the active layer, after the laser-induced graphene material is energized, the laser-induced graphene material punctures a cell membrane of a bacterium with a sharp edge, and carriers in the active layer are electrolyzed to generate electric charges, causing death of the bacterium through its combination with the surface of the active layer, the electric charges, and locally generated hydrogen peroxide toxicity, so that the sterilization structure provided by the present disclosure can prevent bacterial aggregation and achieve a sterilization effect.

In some examples, as shown in FIG. 1 to FIG. 4, the sterilization structure further includes: a source electrode layer 05 and a drain electrode layer 06. The source electrode layer 05 and the drain electrode layer 06 are provided independently of each other, and are respectively electrically connected with the active layer 01. Thus, the sterilization structure can apply a voltage or a current to the active layer through the source electrode layer and the drain electrode layer. For example, by applying a voltage difference to the source electrode layer and the drain electrode layer, a current flows from the source electrode layer to the drain electrode layer; the active layer acts as a supporter of the carriers; a carrier concentration in the active layer may be adjusted by adjusting a magnitude of the applied voltage difference; different carrier concentrations may result in different sterilization effects, so sterilization effects of different strengths can be achieved; the greater the above-described voltage difference, the greater the carrier concentration, and the better the sterilization effect.

In some examples, at least one of the source electrode layer 05 and the drain electrode layer 06 is made of a graphene material. The source electrode layer, the drain electrode layer and a gate electrode layer are all made of a graphene material. Upon at least one of the source electrode layer 05 and the drain electrode layer 06 being made of a graphene material, a small amount of electrons in the graphene material will enter the active layer, so that the carrier concentration can be further increased to improve the sterilization effect. In addition, because the graphene material is an ultra-thin material, upon both the source electrode layer and the drain electrode layer being made of a graphene material, an overall thickness of the sterilization structure can be greatly reduced, so as to reduce a device size of the sterilization structure; then an ultra-thin sterilization structure can be prepared, and the sterilization structure may be applied to fields such as wearable apparatuses, optical detectors and artificial intelligence apparatuses that meet requirements of ultra-thinness, light weight, low power consumption and flexibility.

In some examples, as shown in FIG. 1 to FIG. 4, the source electrode layer 05 includes a first connecting portion 051 connected with the active layer 01, the drain electrode layer 06 includes a second connecting portion 061 connected with the active layer 01; an orthographic projection of at least one of the first connecting portion 051 and the second connecting portion 061 on the active layer 01 falls into the exposed region A. That is to say, at least one of the first connecting portion 051 and the second connecting portion 061 can be prevented from covering the active layer 01 by being disposed on a side of the active layer 01 close to a substrate 02, so that an area of the exposed region A can be enlarged.

In some examples, as shown in FIG. 1 to FIG. 4, the sterilization structure further includes: a substrate 02, a gate electrode 03 and a gate insulating layer 04; the gate electrode 03 being located on the substrate 02, and the gate insulating layer 04 being disposed on a side of the gate electrode 03 away from the substrate 02. The active layer 01 is located on a side of the gate insulating layer 04 away from the gate electrode 03, and an orthographic projection of the active layer 01 on the substrate 02 at least partially overlaps with an orthographic projection of the gate electrode 03 on the substrate 02. At this time, the gate electrode 03, the gate insulating layer 04, the active layer 01, the source electrode layer 05 and the drain electrode layer 06 may constitute one thin film transistor 100, the surface of the active layer 01 includes the exposed region A, and the active layer 01 is made of a laser-induced graphene material.

The sterilization structure provided by the embodiment of the present disclosure includes a thin film transistor, the thin film transistor includes the active layer, the surface of the active layer has the exposed region, and the active layer is made of a laser-induced graphene material. In the present disclosure, the active layer of the thin film transistor is fabricated with a laser-induced graphene material; in the exposed region of the active layer, after the laser-induced graphene material is energized, laser-induced graphene punctures a cell membrane of a bacterium with a sharp edge, and carriers in the active layer are electrolyzed to generate electric charges, causing death of the bacterium through its combination with the surface of the active layer, the electric charges, and locally generated hydrogen peroxide toxicity, so that the sterilization structure provided by the present disclosure can prevent bacterial aggregation and achieve the sterilization effect.

It should be noted that, the laser-induced graphene material is obtained by burning flexible polyimide tablets with laser, which are thus turned into graphene slices whose surfaces are interconnected, that is, laser-induced graphene (LIG). Laser-induced graphene can prevent biofouling and prevent accumulation of microorganisms, plants or other biological materials on a wet surface. In addition, laser-induced graphene is extremely resistant to formation of biomembrane; and the material, when energized, can kill bacteria.

For example, the above-described sterilization structure provided by the embodiment of the present disclosure may be combined with a transparent display or a flexible display, to enhance deep application of the display; for example, the sterilization structure, when combined with the transparent display, may be fabricated into a disinfection storage door, for example, a refrigerator door and a door of a cultural relic exhibition hall, etc.; the sterilization structure, when combined with the flexible display, may be used in a sterilization device applicable to a wearable apparatus; and the sterilization structure, when combined with a sensor, may be applied to biological control, sewage treatment, and other engineering. Therefore, the above-described sterilization structure provided by the embodiment of the present disclosure can implement sterilization treatment of different strengths in different regions, which is of great significance for cultural relic protection, sewage treatment, and biomedicine.

For example, in the above-described sterilization structure provided by the embodiment of the present disclosure, as shown in FIG. 1 to FIG. 4, by applying a voltage to the gate electrode layer, a current flows from the source electrode layer to the drain electrode layer; the active layer acts as the supporter of the carriers; the carrier concentration in the active layer can be adjusted by adjusting the magnitude of the applied voltage; different carrier concentrations may result in different sterilization effects, so the sterilization effects of different strengths can be achieved; the larger the voltage, the greater the carrier concentration, and the better the sterilization effect.

Figure 2:
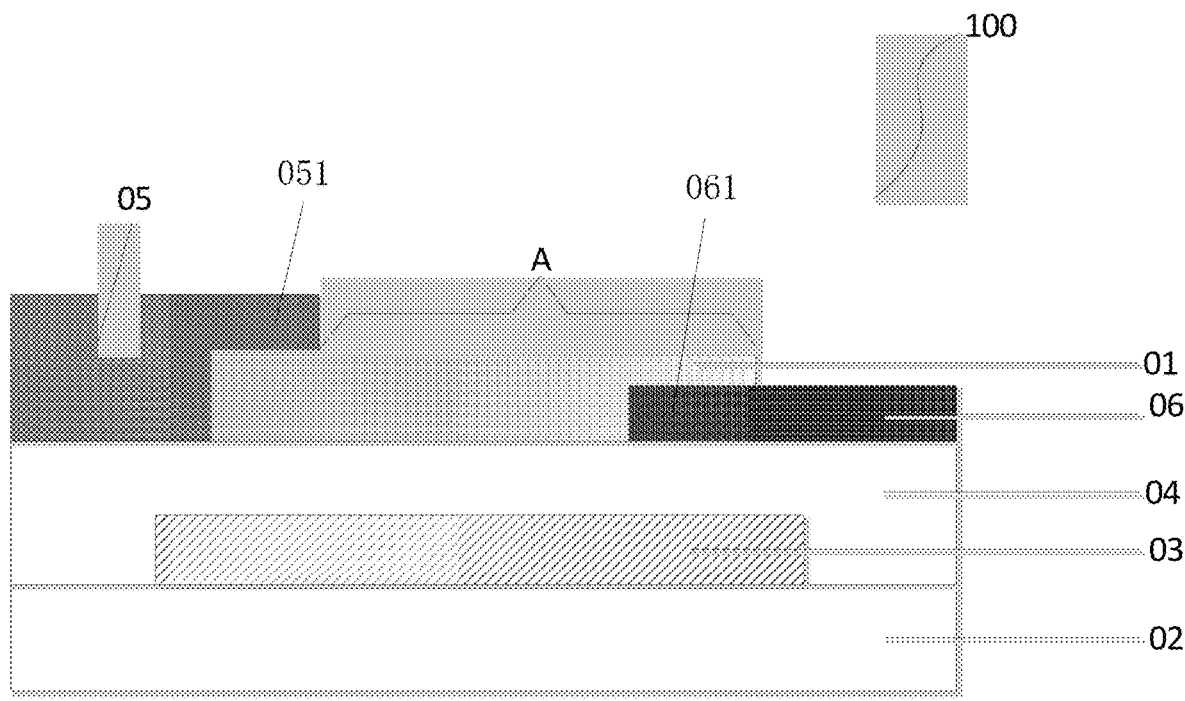
FIG. 2 is a structural schematic diagram of another sterilization structure provided by an embodiment of the present disclosure.

For example, in the above-described sterilization structure provided by the embodiment of the present disclosure, as shown in FIG. 1 and FIG. 2, the source electrode layer 05 and the drain electrode layer 06 are disposed in different layers. In this way, the exposed region A of the active layer 01 is larger, which further enhances sterilization ability.

For example, in the above-described sterilization structure provided by the embodiment of the present disclosure, as shown in FIG. 1, the source electrode layer 05 is located between the active layer 01 and the gate insulating layer 04, and the drain electrode layer 06 is located on a side of the active layer 01 away from the gate insulating layer 04; or as shown in FIG. 2, the source electrode layer 05 is located on the side of the active layer 01 away from the gate insulating layer 04, and the drain electrode layer 06 is located between the active layer 01 and the gate insulating layer 04. At this time, by applying a voltage to the gate electrode layer 03, a current flows from the source electrode layer 05 to the drain electrode layer 06, which is surface transmission (indicated by dotted arrows), the active layer 01 acts as the supporter of the carriers, and surface transmission can adjust the carrier concentration in the active layer 01, to implement sterilization effects of different strengths.

For example, as shown in FIG. 1, the first connecting portion 051 is located between the active layer 01 and the gate insulating layer 04, and the second connecting portion 061 is located on the side of the active layer 01 away from the substrate 02.

For example, as shown in FIG. 2, the first connecting portion 051 is located on the side of the active layer 01 away from the substrate 02, and the second connecting portion 061 is located between the active layer 01 and the gate insulating layer 04.

Figure 3:
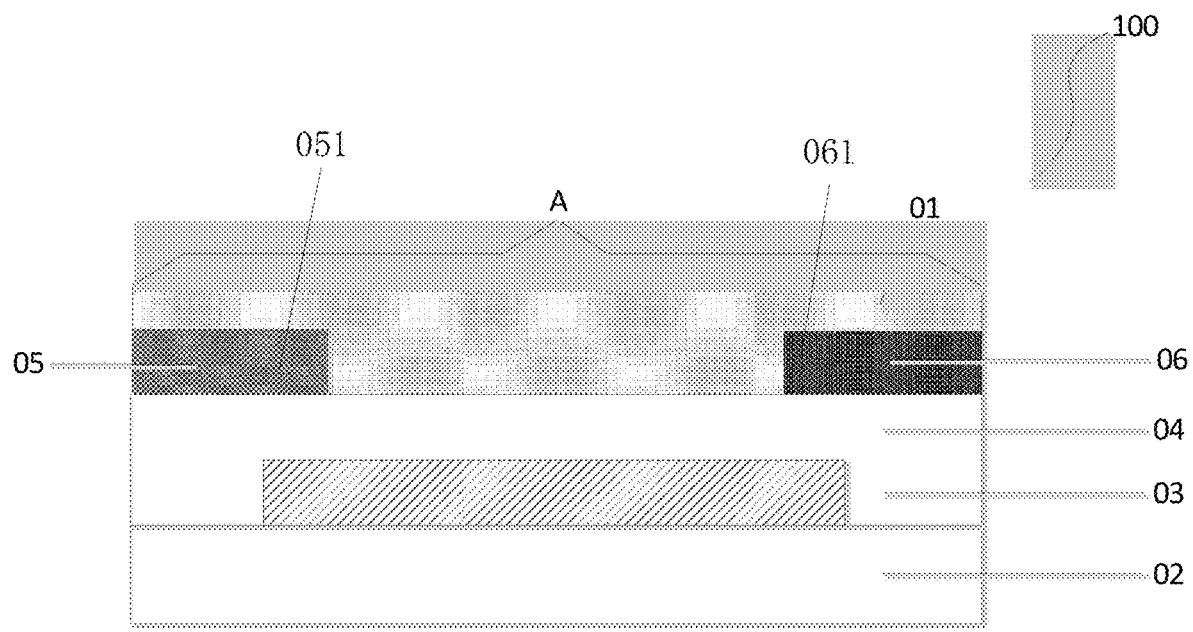
FIG. 3 is a structural schematic diagram of still another sterilization structure provided by an embodiment of the present disclosure.
Figure 4:
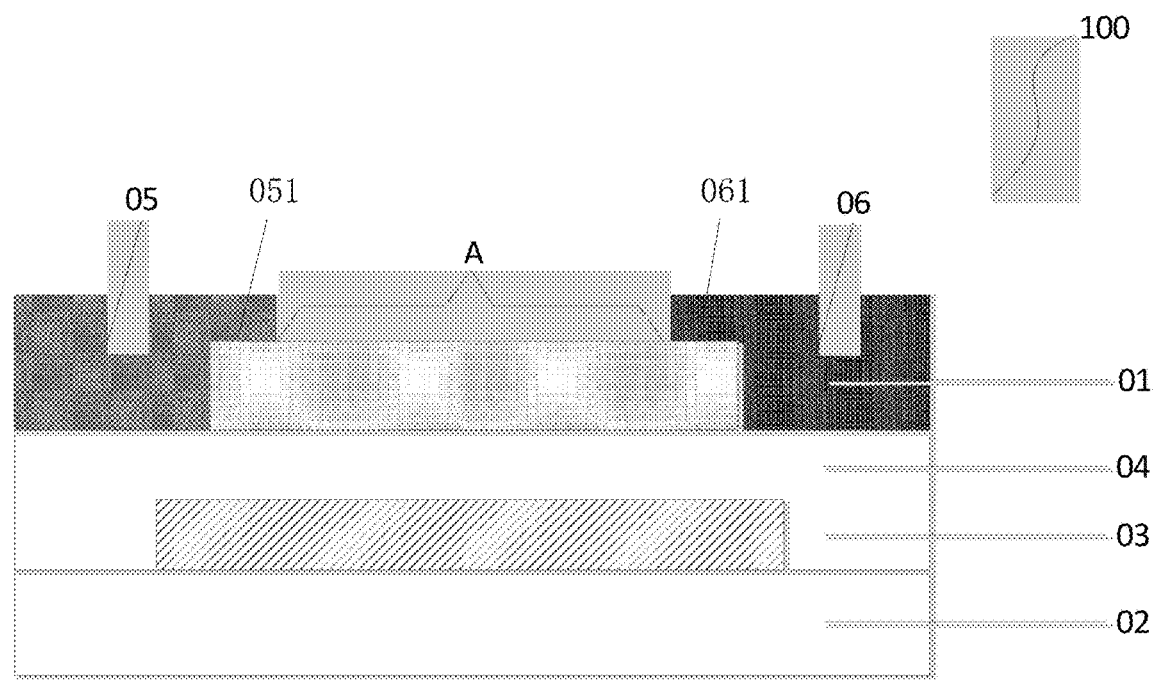
FIG. 4 is a structural schematic diagram of yet another sterilization structure provided by an embodiment of the present disclosure.

For example, in the above-described sterilization structure provided by the embodiment of the present disclosure, as shown in FIG. 3 and FIG. 4, the source electrode layer 05 and the drain electrode layer 06 may also be provided in a same layer. For example, as shown in FIG. 3, the first connecting portion 051 and the second connecting portion 061 are both located between the active layer 01 and the gate insulating layer 04, so that the exposed region A of the active layer 01 can be further enlarged, which further enhances the sterilization ability.

For example, in the above-described sterilization structure provided by the embodiment of the present disclosure, as shown in FIG. 3, since the larger the exposed region A, the better the sterilization effect, in order to further enlarge the exposed region A of the active layer 01, the source electrode layer 05 and the drain electrode layer 06 are both provided between the active layer 01 and the gate insulating layer 04; or as shown in FIG. 4, the source electrode layer 05 and the drain electrode layer 06 are both located on the side of the active layer 01 away from the gate insulating layer.

For example, the thin film transistor 100 included by the sterilization structure shown in FIG. 1 to FIG. 4 provided by the embodiment of the present disclosure has a bottom gate type structure; of course, when specifically implemented, the thin film transistor 100 may also have a top gate type structure; if the thin film transistor 100 has the top gate type structure, the substrate 02 of the thin film transistor 100 is a flexible substrate, so after the thin film transistor 100 is fabricated, it is necessary to strip the flexible substrate from the active layer 01 of the thin film transistor 100, so that the active layer 01 has the exposed region A, to further implement the sterilization function.

For example, in the above-described sterilization structure provided by the embodiment of the present disclosure, as shown in FIG. 1 to FIG. 4, a region of the surface of the active layer 01 that is not covered by the source electrode layer 05 and the drain electrode layer 06 is the exposed region A. Specifically, when the sterilization structure is applied to a display apparatus, in order to ensure that the surface of the active layer 01 has the exposed region A, the thin film transistor included by the sterilization structure is not provided with any other film layer.

For example, in the above-described sterilization structure provided by the embodiment of the present disclosure, the source electrode layer, the drain electrode layer, and the gate electrode layer are all made of a graphene material. Specifically, the source electrode layer is made of a graphene material; when a voltage is applied to the gate electrode layer of the thin film transistor, a small amount of electrons in the graphene material will enter the active layer, so that the carrier concentration can be further increased to improve the sterilization effect; the graphene material is an ultra-thin material, when both the drain electrode layer and the gate electrode layer are made of a graphene material, an overall thickness of the thin film transistor can be greatly reduced to further reduce a thickness of the sterilization structure, so as to reduce a device size of the sterilization structure; then an ultra-thin sterilization structure can be prepared, and the sterilization structure may be applied to fields such as wearable apparatuses, optical detectors and artificial intelligence apparatuses that meet requirements of ultra-thinness, light weight, low power consumption and flexibility.

For example, the substrate provided by the embodiment of the present disclosure may be a flexible substrate, for example, the flexible substrate is made of plastic or resin, etc., specifically, for example, polydimethylsiloxane, etc. The flexible substrate is used so that the sterilization structure is applicable to an electronic apparatus such as a wearable apparatus, an artificial intelligence apparatus, a curved surface, or a bendable apparatus.

For example, the substrate provided by the embodiment of the present disclosure may be a transparent glass substrate, and the transparent glass substrate is used so that the sterilization structure is applicable to a transparent display electronic apparatus.

In some examples, the active layer has a thickness ranging from 20 microns to 25 microns, so as to provide a better sterilization effect.

Figure 5:
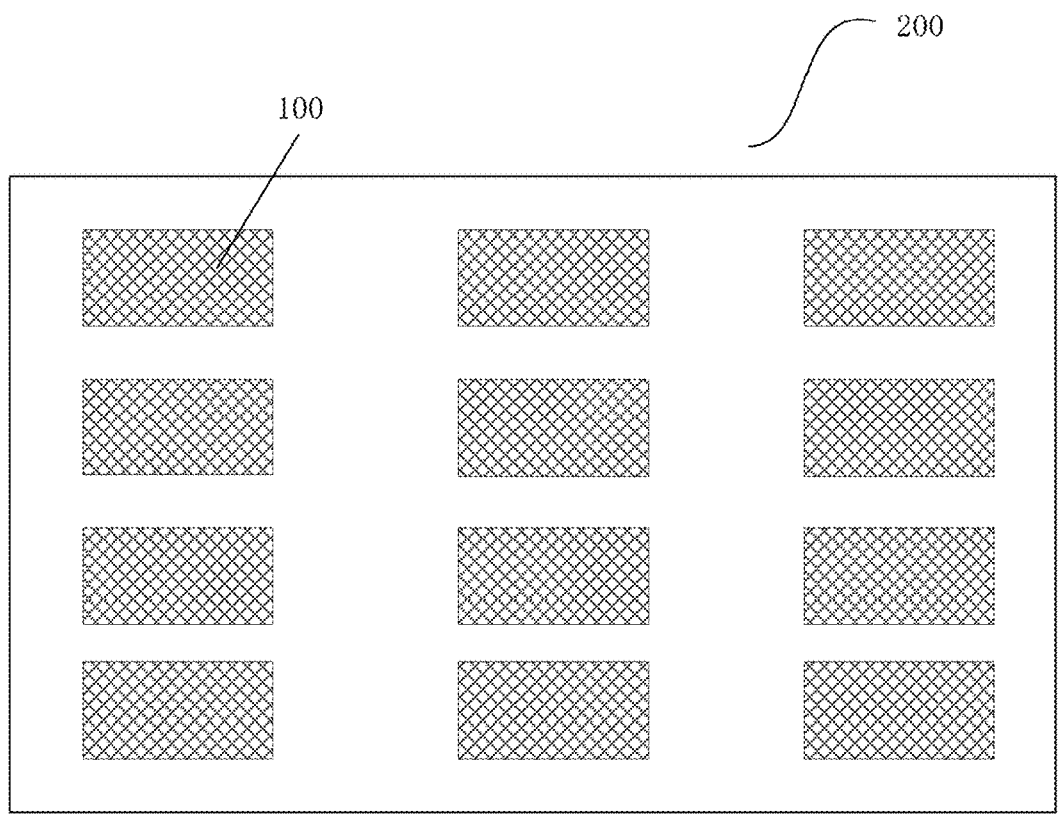
FIG. 5 is a schematic diagram of a sterilization board provided by an embodiment of the present disclosure.

Based on a same inventive concept, an embodiment of the present disclosure further provides a sterilization board, and as shown in FIG. 5, the sterilization board 200 includes a plurality of sterilization structures 100 as described above. The sterilization board has a better sterilization effect, and thus can be used as an inner liner of various electrical appliances (for example, an inner liner of a refrigerator fresh-keeping room), for maintaining cleanliness inside the electrical appliances. In addition, the sterilization board may also be disposed on outer surfaces of various electrical appliances, to prevent the surfaces of the electrical appliances from being contaminated by bacteria.

For example, as shown in FIG. 5, the plurality of sterilization structures 100 are arranged in an array.

Figure 6:
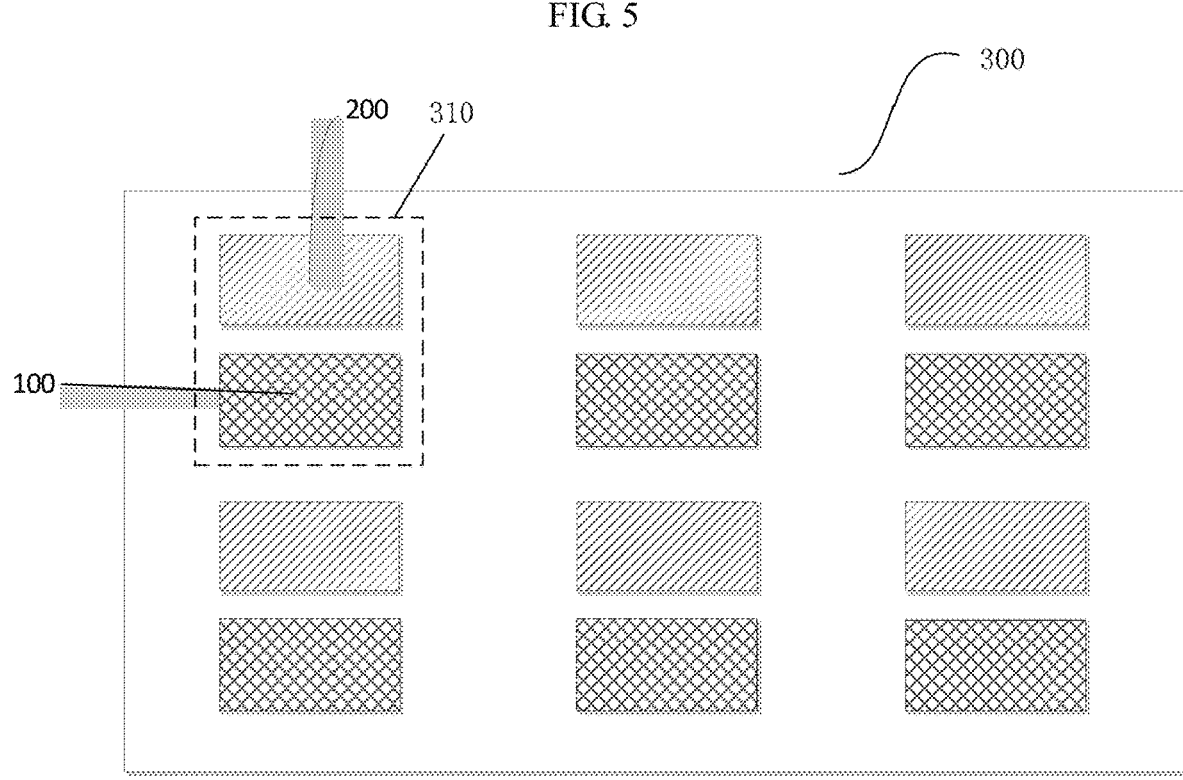
FIG. 6 is a schematic diagram of a display device provided by an embodiment of the present disclosure.

Based on a same inventive concept, an embodiment of the present disclosure further provides a display device, and as shown in FIG. 6, the display device 300 includes a plurality of sterilization display elements 310 arranged in an array, each of the plurality of sterilization display elements 310 includes a display element and the above-described sterilization structure 100. That is to say, the respective sterilization display element 310 each have a display region and a non-display region; the display region includes a switch transistor 200 used for display, the non-display region includes the above-described sterilization structure provided by the embodiment of the present disclosure, and the sterilization structure includes a thin film transistor 100. The thin film transistor 100 and the switch transistor 200 are controlled by different control signals, that is, the two operate independently; specifically, sterilization and display can be performed simultaneously, or sterilization and display may also be performed in a time-sharing manner. A principle on which the display substrate solves problems is similar to that of the above-described sterilization structure, so implementation of the above-described sterilization structure may be referred to for implementation of the display substrate, which will not be repeated here. The sterilization structure, the sterilization board and the display device are provided by the embodiments of the present disclosure; the sterilization structure includes the thin film transistor, the thin film transistor includes the active layer, the surface of the active layer has the exposed region, and the active layer is made of a laser-induced graphene material. In the present disclosure, the active layer of the thin film transistor is fabricated with a laser-induced graphene material, and the surface of the active layer has the exposed region, so that after the laser-induced graphene material is energized, laser-induced graphene punctures a cell membrane of a bacterium with a sharp edge, and carriers in the active layer are electrolyzed to generate electric charges, causing death of the bacterium through its combination with the surface of the active layer, the electric charges, and locally generated hydrogen peroxide toxicity, so that the sterilization structure provided by the present disclosure can prevent bacterial aggregation and achieve the sterilization effect.

The following statements should be noted:

(1) The accompanying drawings involve only the structure(s) in connection with the embodiment(s) of the present disclosure, and other structure(s) can be referred to common design(s).

(2) In case of no conflict, features in one embodiment or in different embodiments can be combined.

The foregoing are merely specific embodiments of the present disclosure, but not limitative to the protection scope of the present disclosure. Within the technical scope disclosed by the present disclosure, any alternations or replacements which can be readily envisaged by one skilled in the art shall be within the protection scope of the present disclosure. Therefore, the protection scope of the invention shall be defined by the accompanying claims.

What is claimed is:

1. A sterilization structure, comprising:
an active layer;
a source electrode layer;
a drain electrode layer;
a substrate;
a gate electrode, located on the substrate; and
a gate insulating layer, located on a side of the gate electrode away from the substrate,
wherein a surface of the active layer comprises an exposed region, and a material of the active layer comprises a laser-induced graphene material,
the source electrode layer and the drain electrode layer are disposed independently of each other, and are electrically connected with the active layer, the exposed region of the surface of the active layer is configured to be in contact with an outside environment and to inhibit or kill bacteria on the exposed region, the exposed region of the surface of the active layer is not covered by the source electrode layer or the drain electrode layer, the active layer is located on a side of the gate insulating layer away from the gate electrode, and an orthographic projection of the active layer on the substrate at least partially overlaps with an orthographic projection of the gate electrode on the substrate, the source electrode layer comprises a first connecting portion connected with the active layer, the drain electrode layer comprises a second connecting portion connected with the active layer, and an orthographic projection of at least one of the first connecting portion and the second connecting portion on the active layer falls into the exposed region, in a direction perpendicular to the substrate, on of the first connecting portion and the second connection portion is located between the active layer and the gate insulating layer, and the other one of the first connecting portion and the second connection portion is located on a side of the active layer away from the substrate.

2. The sterilization structure according to claim 1, wherein at least one of the source electrode layer and the drain electrode layer comprises a graphene material.

3. The sterilization structure according to claim 1, wherein the first connecting portion and the second connecting portion are disposed in different layers.

4. The sterilization structure according to claim 1, wherein materials of the source electrode layer, the drain electrode layer, and the gate electrode all comprise a graphene material.

5. The sterilization structure according to claim 1, wherein the active layer has a thickness ranging from 20 microns to 25 microns.

6. A sterilization board, comprising a plurality of sterilization structures according to claim 1.

7. The sterilization board according to claim 6, wherein the plurality of sterilization structures are arranged in an array.

8. A display device, comprising the sterilization structure according to claim 1.

9. The display device according to claim 8, further comprising:
a plurality of sterilization display elements arranged in an array,
wherein each of the plurality of sterilization display elements comprises a display element and the sterilization structure.

* * * * *